United States Patent [19]

Ionescu et al.

[11] 4,441,216
[45] Apr. 10, 1984

[54] TISSUE HEART VALVE AND STENT

[75] Inventors: Marian I. Ionescu, Leeds, England; Jay A. Lenker, Laguna Beach; Robert F. Rosenbluth, Laguna Niguel, both of Calif.

[73] Assignee: Shiley, Inc., Irvine, Calif.

[21] Appl. No.: 327,081

[22] Filed: Dec. 3, 1981

[30] Foreign Application Priority Data

Oct. 29, 1981 [EP] European Pat. Off. ........ 81305122.4

[51] Int. Cl.³ .............................................. A61F 1/22
[52] U.S. Cl. ......................................................... 3/1.5
[58] Field of Search ......................................... 3/1.5, 1

[56]         References Cited
       U.S. PATENT DOCUMENTS

| 3,197,788 | 8/1965 | Segger | 3/1.5 |
| 3,739,402 | 6/1973 | Cooley et al. | 3/1.5 |
| 4,084,268 | 4/1978 | Ionescu et al. | 3/1.5 |
| 4,172,295 | 10/1979 | Batten | 3/1.5 |
| 4,259,753 | 4/1981 | Liotta | 3/1.5 |
| 4,291,420 | 9/1981 | Reul | 3/1.5 |
| 4,340,977 | 7/1982 | Brownlee et al. | 3/1.5 |
| 4,345,340 | 8/1982 | Rosen | 3/1.5 |
| 4,388,735 | 6/1983 | Ionescu et al. | 3/1.5 |

FOREIGN PATENT DOCUMENTS 1264472 2/1972 United Kingdom .................... 3/1.5

OTHER PUBLICATIONS

"Heart Valve Replacement with Autologous Fascialata" by M. I. Ionescu et al., The Journal of Thoracic & Cardiovascular Surgery, vol. 60, No. 3, Sep. 1970, pp. 331-354.

"Frame-Mounted Tissue Heart Valves: Technique of Construction" by I. T. Bartek et al., Thorax, (1974), 29, 51, pp. 51-55.

Primary Examiner—Ronald L. Frinks
Attorney, Agent, or Firm—Knobbe, Martens, Olson & Bear

[57]                ABSTRACT

An improved stent for prosthetic tissue heart valves having upright legs which have radiused upper tips which are approximately one-half the width of prior art stent legs is disclosed. These narrow tipped stent legs reduce stress induced in the leaflets by curvature of the leaflets around the tips of the stent legs in the closed position, extending the service life of the valve. Tabs are added to the tips of the stent legs to add structural strength. These tabs can be tapered or straight but their bottom portions must be narrower than the stent leg. The tabs have a plurality of holes in them through which coaptation stitches are passed. The coaptation stitch can be two separate stitches, one in a first plane and one in a second plane at 90° to the first plane, or, in the preferred embodiment, a single figure eight stitch passing through the holes in the tab in a plane coincident with the long axis of the stent leg.

17 Claims, 14 Drawing Figures

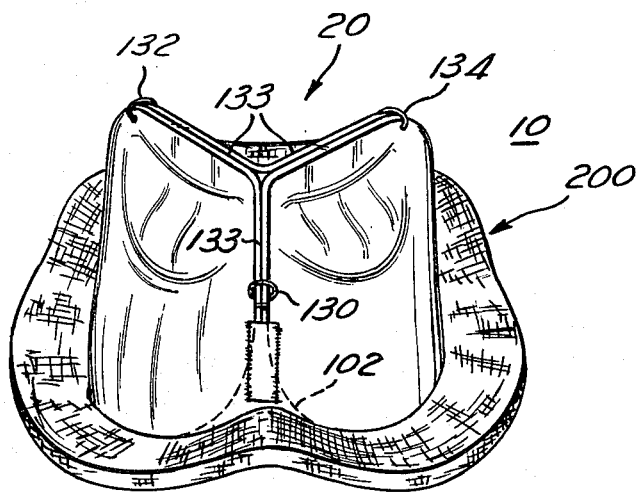
Fig. 1
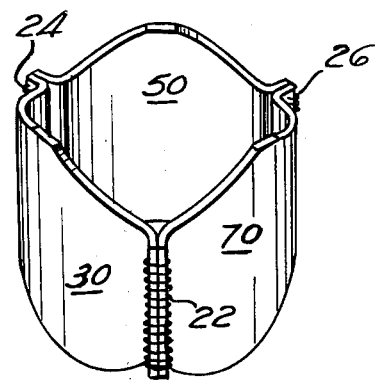
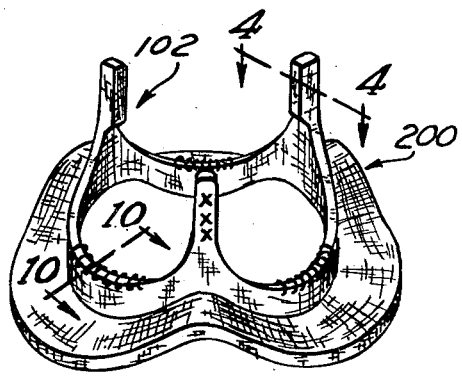
Fig. 2
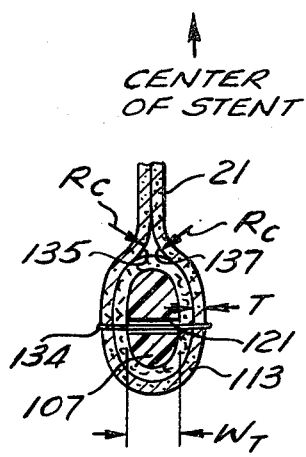
Fig. 4
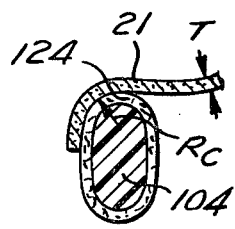
Fig. 10

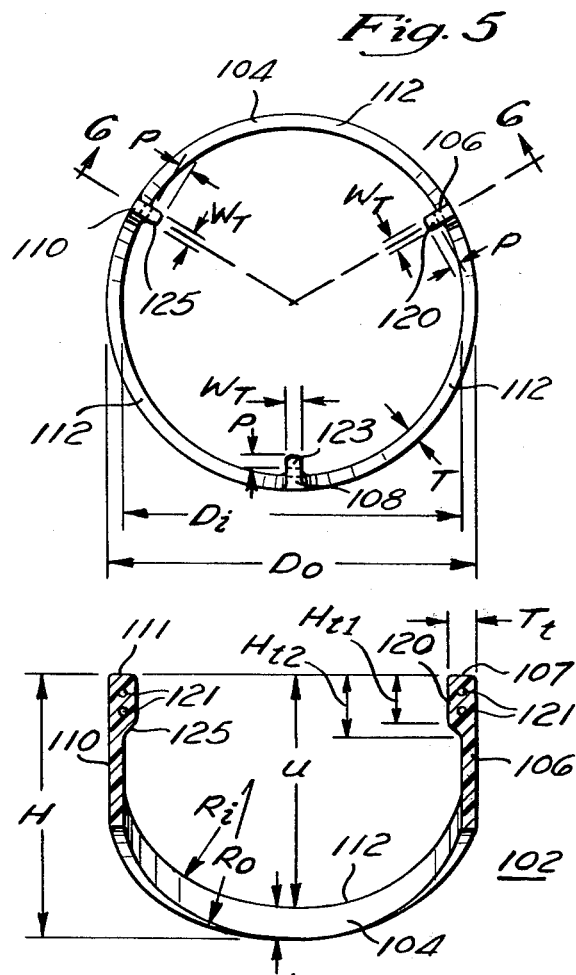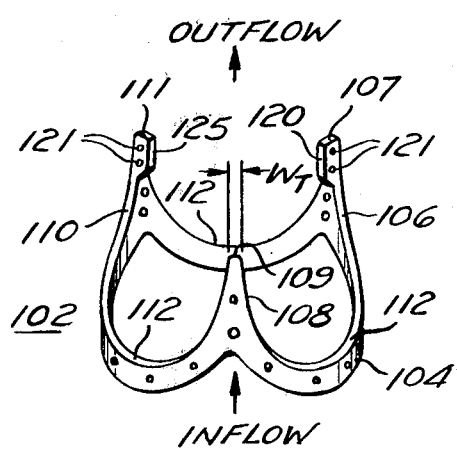

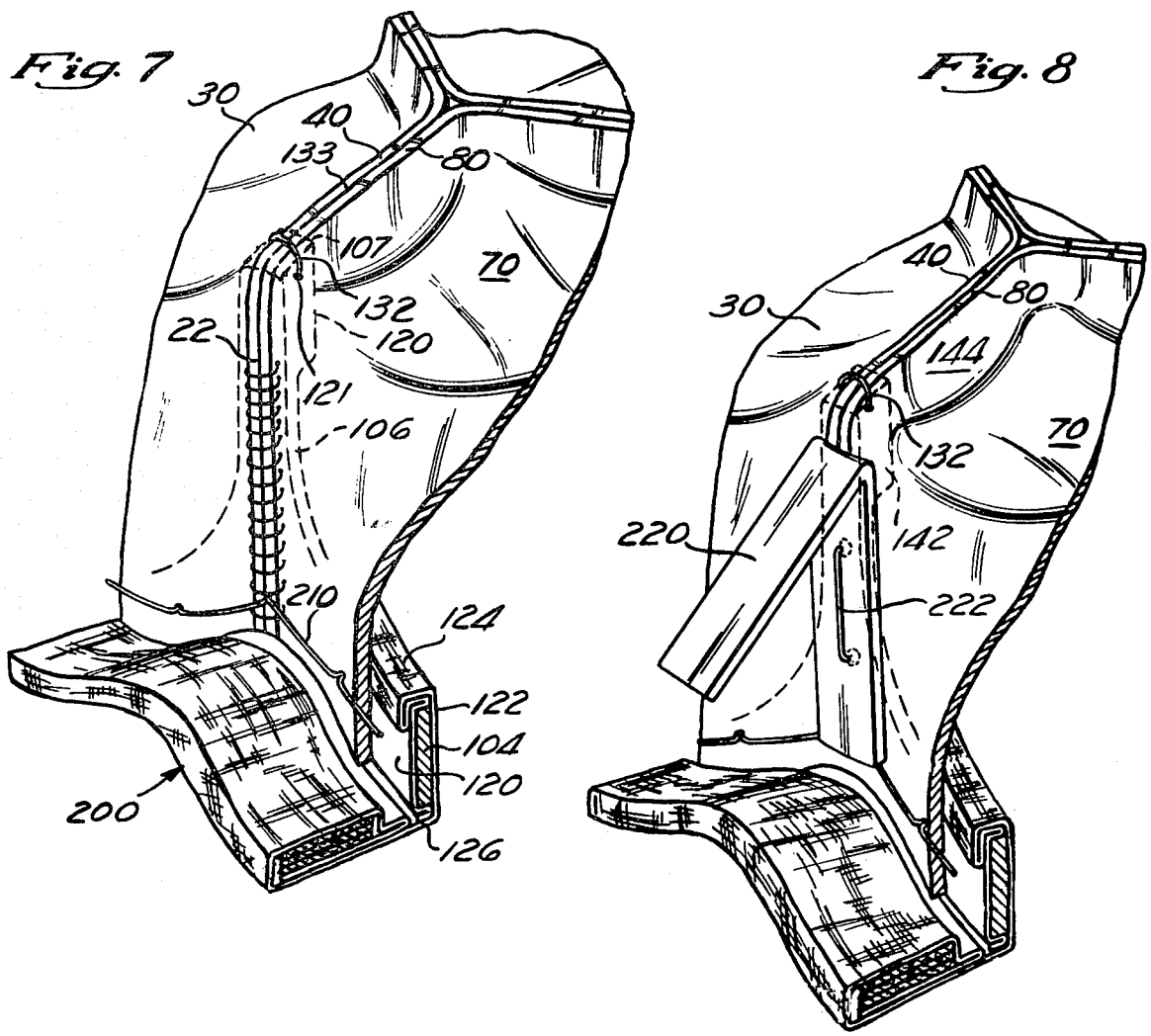
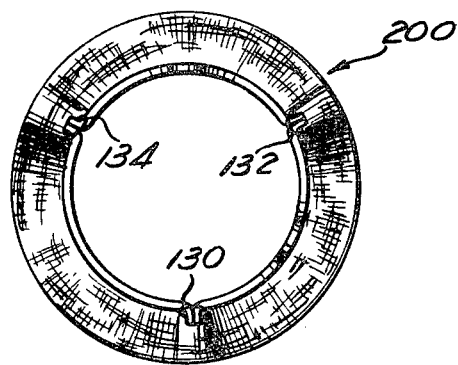

TISSUE HEART VALVE AND STENT

TECHNICAL FIELD

The early development of prosthetic heart valves is well documented in papers given at symposia in 1960 and in 1968, published in Prosthetic Heart Valves, Lyman A. Brewer, III, Ed., Charles C. Thomas Publishing Co., Springfield, Ill. (1969), Second National Conference on Prosthetic Heart Valves; Prosthetic Valves For Cardiac Surgery, K. Alvin Merendino, Editor, Thomas Publishing Co., Springfield, Ill. (1961).

Lefrak and Starr recently surveyed the development of cardiac valve prostheses, E. A. Lefrak, and A. Starr, Cardiac Valve Prostheses, Appleton-Centry-Krofts, N.Y., 1979 and the development of tissue heart valves has been comprehensively reviewed by Ionescu, Marian I., Tissue Heart Valves, Butterworths, Boston, 1979.

Great efforts have been expended in the development of tissue heart valve prostheses and in the development of supportive structures, or stents, for tissue valves. Representative of efforst to develop stents for tissue valves are the disclosures in the following U.S. Patents: U.S. Pat. No. 3,570,014, W. D. Hancock, Mar. 16, 1971; U.S. Pat. No. 3,714,671, William Sterling Edwards, et al, Feb. 6, 1973; Pat. No. 3,755,823, W. D. Hancock, Sept. 4, 1973; U.S. Pat. No. 3,983,581, William W. Angell, Oct. 5, 1976; U.S. Pat. No. 4,035,849, William W. Angell et al, July 19, 1977; U.S. Pat. No. 4,079,468, Domingo Santo Liotta, Mar. 21, 1978; U.S. Pat. No. 4,084,268, Marian I. Ionescu et al, Apr. 18, 1978; U.S. Pat. No. 4,106,129, Alain F. Carpenter, et al, Aug. 15, 1978; U.S. Pat. No. 4,172,295, Richard J. Batten, Oct. 30, 1979 and U.S. Pat. No. 4,192,020, Richard B. Davis, et al, Mar. 11, 1980. Other structures are also reported in the aforementioned treatises on heart valve developments.

A number of specific tissue valves are described in the following publications:

W. Sterling Edwards, et al, Mitral and Aortic Valve Replacement with Fascia Lata on a Frame, Journal of Thoracic & Cardiovascular Surgery, Volume 58, No. 6, December 1969, Pages 854–858; Ionescu, M. I., et al, Heart Valve Replacement with Ionescu-Shiley Pericardial Xenograft, Caridology Digest, June, 1977, Page 45: Ionescu, M. I., et al, Heart Valve Replacement with the Ionescu-Shiley Pericardial Xenograft, The Journal of Thoracic and Caridovascular Surgery, Volume 73, Pages 31–42, 1977; Tandon, A. P., et al, Long-Term Haemodynamic evaluation of aortic pericardial xenograft, British Heart Journal, Volume 40, Pages 602–607, 1978; Ionescu, M. I. et al, Long-Term Clinical and Haemodynamic Evaluation of the Ionescu-Shiley Pericardial Xenograft Heart Valve, Thoraxchirurgie, Volume 26, Pages 250–258, 1978; Ionescu, M. I. et al, Long-Term Sequential Hemodynamic Evaluation of Right Ventricular Outflow Tract Reconstruction using a Valve Mechanism, The Annals of Thoracic Surgery, Volume 27, No. 5, May, 1979; Ross, D. N., Flexible Bioprosthetic Pericardial Hart Valve, Thoracic & Cardiovascular Surgery, Volume 28, Pages 150-152, 1980.

Particular techniques for preparing, handling and storing tissue valves are disclosed in U.S. Pat. No. 3,966,401, Hancock et al, June 29, 1976, and U.S. Pat. No. 4,182,446, Penny, January 1980.

Some of the earliest heart valve prostheses were flexible two-or three-cusp valves in which the cusps were constructed of various types of fabric. Some of these flexible leaflet valves had good flow characteristics but most failed early. The leaflets tore, separated from the annulus, or became rigid due to fibrous tissue ingrowth. From about 1960 into the 1970's the trend was to mechanical valves. These ranged from the mechanically quite simple Starr-Edwards valve to the relatively sophisticated Bjork-Shiley valve and included a number of disc poppet valves. These mechanical valves generally dominated the market and are still very satisfactory for many applications. Tissue valves are still the preferred treatment where anticoagulation therapy is not tolerated by the patient.

In 1962, Donald Ross and Sir Brian Barratt-Boyes, independently, were performing implantations of homograft tissue valves some of which were free graft implants and some were mounted on supporting stents. Fully clothed covered rigid stents were used in some of these homograft valves.

In 1965, Drs. Binet and Carpentier, and their associates, implanted a specially prepared porcine aortic valve xenograft. These porcine valves were sterilized and treated, e.g. with formaldehyde, and were commonly attached to a metal stent. Experience showed that these valves were of short life, largely because formaldahyde was used as the cross-linking agent. Formaldehyde was found to create reversible cross links in the tissue, thereby allowing early breakdown of the tissue. Dr. Carpentier, in about 1968, established the concept of the bioprosthesis by substantially eliminating antigenicity of the tissue, principally by changing the preservative from formaldehyde to glutaraldehyde. Glutaraldehyde has been shown to create cross links of a more permanent nature than those created by formaldehyde.

A number of porcine bioprostheses and specially designed stents for supporting these protheses resulted from the efforts of Warren Hancock et al. Generally, pig aortic valves are procured under clean conditions, placed in a cold, balanced electrolyte solution, excess tissue is trimmed and the xenografts are immersed in 0.2% glutaraldehyde. The leaflets are held in their normal valving postion under pressure during the tanning process and each valve is sutured to a cloth covered stent by multiple sutures. A number of designs and stent constructions for the Hancock type valve are exemplified in the aforementined U.S. Pat. Nos. 3,570,014 and 3,755,823. Stents for porcine valves were developed by a number of other workers also, see, e.g., U.S. Pat. Nos. 3,983,581; 4,035,849; 4,079,468 and 4,106,129.

Stents for supporting cusp valves of other tissue members, e.g. fascia lata and pericardium, have been developed by a number of workers, see, e.g., U.S. Pat. No. 3,714,671, and Edwards et al, Mitral and Aortic Valve Replacement with Fascia Lata on a Frame, supra. Much of the pioneering work in this area of valve development was done by Mr. Marian I. Ionescu and his associates, see, e.g., Bartek, et al, Frame-Mounted Tissue Heart Valves: Technique of Construction, Thorax, Volume 29, Pages 51–55, 1974; Ionescu, et al, Heart Valve Replacement with Ionescu-Shiley Pericardial Xenograft, Cardiology Digest, June, 1977; Ionescu, et al, Heart Valve Replacement with Ionescu-Shiley Pericardical Xenograft, The Journal of Thoracic and Cardiovascular Surgery, Volume 73, Pages 31–42, 1977; Tandon, et al, Long-Term Haemodynamic Evaluation of Aortic Pericardial Xenograft, British Heart Journal, Volume 40, Pages 602–607, 1978; Ionescu, et al, Long-term Clinical and Haemodynamic Evaluation of the Ionescu-Shiley Pericardial Xenograft Heart Valve, Thoraxchirugie, Volume 25, Pages 250-258, 1978; Ionescu, et al, Long-term Sequential Hemodynamic Evaluation of Right Ventricular Outflow Tract Reconstruction Using A Valve Mechanism, The Annals of Thoracic Surgery, 27, 425,434, 1979; and Ionescu, Editor, Tissue Heart Valves, Butterworths, 1979.

A number of improvements in the basic Ionescu tissue heart valve have been made. For example, a tissue heart valve has been developed which has a cloth-covered stent of special construction, in which the outflow annulus diameter of the valve is defined and limited by the positioning of a coaptation stitch on the inside of the supporting legs of the stent, as has been the practice since the early development of the Ionescu type tissue heart valve. Another improvement in the method for aligning the tissue of the cusps of the Ionescu type heart valve is described in U.S. Pat. No. 4,172,295 which also disclosed the coaptation stitch inside the stent legs.

A potential problem remains, however, in that stress is concentrated in the tissue in some areas where sharp bending of the tissue around the stent occurs. Some measures can be taken to relieve this stress. The stress tends to be highest at points of maximum curvature such as around the tips of the stent legs because of the pinching of the tissue leaflets together inside and above the tip of the stent leg.

These problems are largely or entirely solved by the present invention.

DISCLOSURE OF THE INVENTION

A significant feature of the present invention resides in the configuration of the stent legs wherein the ratio defined as the value of the radius of curvature of tissue around the inside top of said leg measured at the point of greatest curvature divided by the thickness of the tissue is approximately five or more. The width of the post top is approximately from 0.760 to 1.05 millimeters and the width of the cloth covered post top is approximately 2 millimeters. The tissue thickness in the preferred embodiment is approximately 0.3 millimeters. The tissue does not pinch together inside such narrow posts during closure at physiological pressure and an inside radius of curvature equal to or greater than 1.5 millimeters is obtained. The life of a valve using such a stent will be extended beyond that of a valve with a smaller radius of curvature.

The improved stent is also designed so that the ratio of the radius of curvature of the tissue around the fabric-covered stent at a point between the upright stent legs divided by the thickness of the tissue is greater than or equal to five.

Additional strength to the legs is provided by inwardly projecting tabs which are, preferably, integrally formed at the tips of the legs, conforming to the width of the stent legs at their tips but narrower than the stent legs at the bottom of the tabs said tabs extending both vertically down the leg for a predetermined distance and inwardly toward the center axis of the stent. Apertures are formed in the tabs through which the coaptation stitches pass to register the coaptation stitch directly above the stent leg.

The coaptation stitches can be in either of two embodiments. The first embodiment consists of two separate stitches, one passing through one aperture in the tab and defining a plane generally parallel to the long axis of the stent legs and tied off above the tips of the stent legs, and the other stitch passing through another aperture in the tabs and defining a plane which is generally perpendicular to the plane defined by the first stitch, said second stitch being tied off at the outside edge of the stent leg. The second embodiment of the coaptation stitch is a single stitch passing through a plurality of holes in the tabs which defines a plane which is parallel to the long axis of the stent leg. The second embodiment is the preferred embodiment and generally defines a figure eight pattern through a pair of holes in each tab.

The inward projection of the tabs toward the center of the aperture is also limited to prevent touching between the tissue leasflets and the bottom of the tabs. Generally this distance of inward projection is limited to forty thousandths of an inch in the naked stent, i.e., no more than forty thousandths inward projection of the bare plastic tab. The width of the tabs is also limited to aid in preventing the bottoms of the tabs from touching the tissue leaflets. In the preferred embodiment, the widths of the tabs remains constant throughout their length while the widths of the stent legs increases at points farther from the tips of the stent legs. In another embodiment, the width of the tab decreases at points further from the tips of the stent legs irrespective of the widths of the stent legs.

BRIEF DESCRIPTION OF THE DRAWINGS

FIG. 1 is an overall perspective view of the completed valve.

FIG. 2 is an exploded view of the cloth covered stent and the valve element formed of three leaflets prior to attachment to the stent.

FIG. 3 is a perspective view of the improved stent configuration.

FIG. 4 is a sectional view of the curvature of tissue around the covered stent leg taken along line 4—4 in FIG. 2.

FIG. 5 is a top view of the stent shown in perspective in FIG. 3.

FIG. 6 is a sectional view taken along section line 6—6 in FIG. 5.

FIG. 7 is a partial perspective view of the coaptation of the tissue leaflets with the stent leg and coaptation stitch.

FIG. 8 is another partial perspective showing the view of FIG. 7 in a later stage of completion.

FIG. 9 is a top view of the completed valve in the fully open position.

FIG. 10 is a sectional view of the curvature of tissue around the stent taken along section line 10—10 in FIG. 2.

DETAILED DESCRIPTION OF THE PREFERRED EMBODIMENT

Figure 12:
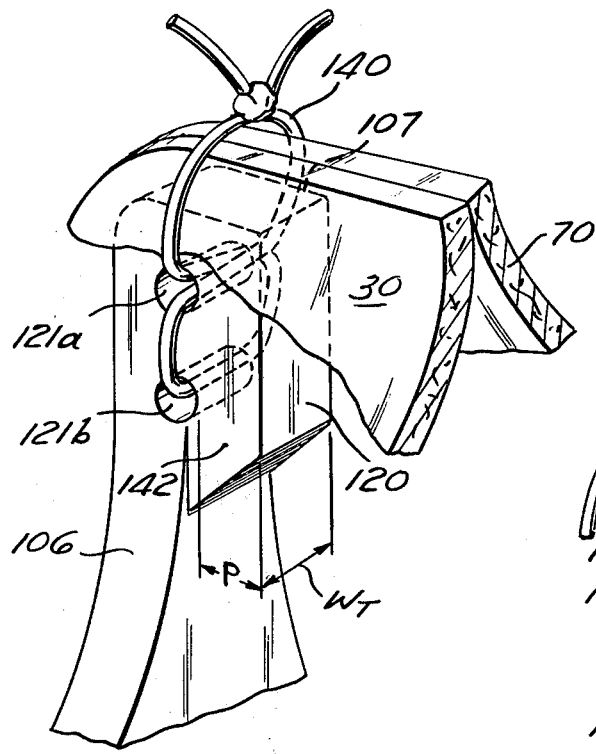
FIG. 12 is a detailed view of the preferred embodiment of the coaptation stitching.

FIG. 1 shows a low profile pericardial xenograft heart valve 10 which comprises a valving element 20, a stent assembly 102 and a suture or sewing ring assembly 200. The coaptation stitches 130, 132, and 134 cause coaptation or joining of the edges of the tissue leaflets of valving element 20 in the vicinity of the tips of said stent legs thereby forming radial coaptation lines 133 in FIG. 1.

FIG. 2 depicts an exploded view of the tissue valving element 20 prior to attachment of the stent 102, and generally shows the three stitch seams 22, 24 and 26 which join the three leaflets 30, 50 and 70 into a right cylindrical valving element. This valving element is then sewn to the cloth-covered stent 102.

The stent 102 shown in FIGS. 3, 5 and 6 includes an annular base or ring 104 with scallops 112 formed therein which defines the flow orifice of the valve. Coupled to the ring or integrally formed therewith are a plurality of stent legs extending upwardly a distance H toward the outflow end of the valve from the lowermost portion of the base. There are three substantially identical legs 106, 108 and 110, each separated from its neighboring legs by a scallop 112 as best shown in FIG. 3. The bottom or inflow edge of the stent 102 is also scalloped to conform generally to the arc of the scallops between the legs. These bottom scallops generally follow the configuration of the scallops 112 of the outflow edge so as to generally form parallel edges defining ring or base 104. The scallops of the lower or inflow edge of the base and the scallops of the outflow edge between the legs vertically define three generally elliptically shaped one-third portions of the base between the centerlines of the respective upright legs which together circumferentially form a right cylinder of constant diameter having an inside diameter $D_i$ with the legs extending parallel to the axis of the cylinder as shown in FIG. 5.

The stent assembly in the preferred embodiment is used with a fabric covering which totally or at least substantially encloses the stent as shown in FIG. 2. It is not essential to the functioning of the present valve that the stent be cloth-covered, but it has been long recognized that there are structural and biological advantages to a fully cloth-covered valve and fully cloth-covered stents for supporting tissue valves. This concept predates the present invention and constitutes no part thereof but is simply adopted a part of the best mode in carrying out the present invention. The fabric covering described in detail by Ionescu et al in U.S. Pat. 4,084,268 (hereinafter '268) has been generally adopted, and the same techniques are applied in the present valve as are taught there except for the improvements disclosed herein. Reference is made to the '268 patent for specific details of the fabrics, knots, sewing and techniques, and the teachings of the '268 patent are incorporated herein by reference. It is sufficient here to describe the stent assembly as including a cloth covering which encloses or substantially encloses and conforms to the stent.

FIG. 7 is a partial cross-section depicting a fabric 120 enclosing the outside of the stent ring 104, a fabric 122 which encloses the inside of the stent ring 104, and seam area 124 which joins the fabrics along the top or outflow edge of the stent. A fabric 126 is joined along the lower edge of the stent and extends outwardly forming part of and attaching to a sewing or suture ring 200.

Sewing ring 200 extends outwardly circumferentially forming an annulus vertically following the scalloped curvature of the base 104 of the stent. It serves the purpose of providing a place that the surgeon may anchor his sutures in when sewing the valve into its position in the heart. This suture ring may be in any of the forms used in the prior art.

The tissue leaflets, after being sewn to form a cylinder as shown in FIG. 2, may be sewn to the stent assembly in any conventional manner, as, for example, by running stitches shown at 210 in FIG. 7.

FIG. 7 depicts the valve in partially completed configuration with the tissue leaflets 30 and 70 joined by seam 22, the upper edges 80 and 40 substantially touching. Coaptation stitch 132 is disposed directly over the tip 109 of the stent leg 108 and passes through a hole 121 in the tab 120 to form the radial coaptation line 133.

FIG. 8 shows another stage in the construction of the valve shown in FIG. 7 by the addition of the pledget and cover 220. This cover is sewn by stitches 222 to the stent legs through the tissue as described by Ionescu et al in U.S. Pat. 4,084,268; or it can be connected in any other convenient manner. The inclusion of the fabric covering, the pledget, and the sewing, all as disclosed with great particularity by Ionescu et al, supra, are utilized in carrying out the invention in its preferred embodiment but they are not part of the invention per se.

Coaptation of the tissue leaflets is caused by the action of coaptation stitches 132, 134 and 130 shown in FIG. 1. This coaptation is defined generally by the placement of the coaptation stitches 130, 132, and 134 directly above the tips 107, 109 and 111 of the stent legs 106, 108 and 110. In prior valves such as the valve disclosed in U.S. Pat. No. 4,084,268, the coaptation stitch had been placed inside the circumference of the circle defined by the tips of the stent legs. Placement of the coaptation stitch directly above the tips of the stent legs tends to allow the orifice diameter of the fully open valve to equal the inside diameter of the covered stent. FIG. 9 illustrates a tissue valve in the fully open position.

It would be advantageous to use the present invention in the valve described in the U.S. Pat. No. 4,388,735 issued on June 21, 1983. Such a use is included in the preferred method of valve construction using the inventive stent; however, the present invention will work in other valves as well.

An improved stent design for tissue heart valves is depicted in FIGS. 3, 5 and 6. FIG. 3 shows the improved stent in perspective. FIG. 5 shows a top view of the stent, and FIG. 6 is a sectional view of the stent taken along section line 6—6 in FIG. 5.

The width $W_t$ of the stent legs 106, 108 and 110 at their tips 107, 109 and 111 in FIG. 5 is substantially less than the width of the tips of prior art stent legs. As shown in FIG. 4 which is a detailed view of the tip of one stent leg, the width $W_t$ is equal to the diameter of the half circle defining the tip if the tip is rounded. In other embodiments where the tip is not rounded then $W_t$ is measured between the points near the tip where the edges of the stent legs first start to curve in toward the center line of the stent leg.

In the preferred embodiment, the stent legs are rounded at their tips. The width of the stent legs at the tips thereof has been reduced from approximately 2.032 millimeters in prior stents to a substantially narrower range of widths from about 0.76 mm to about 1.14 mm. This reduced width of the stent legs at their tips has the effect of increasing the radius of curvature of the tissue inside the stent leg and tip. This curvature is caused by the action of the coaptation stitches 132, 130 and 134 in FIG. 1 and by closure of the valve which causes collapse of the cusps 30, 50 and 70 toward the center of the valve under the restriction of the coaptation stitches.

That is, the tissue leaflets 30, 50 and 70 curve less sharply together at the tips 107, 109 and 111 of the stent legs where the tips of the legs are narrower. This increased radius of curvature translates into reduced stress in the tissue of the cusps and a longer service life for the valve.

However, this reduced width of the tips of the stent legs 106, 108 and 110 in FIG. 3 leaves less material in the stent legs to carry the structural loading of the closed leaflets caused by the impulse pressure in the flow of blood caused by intermittent pumping action of the heart. To compensate for the reduced width in the leg tips, tabs 120, 123 and 125, FIGS. 3 and 5 are added at the outflow end or tip of each of the stent legs to add structural strength to the legs. These tabs preferably project inwardly toward the center of the stent and are integrally formed with the stent legs and preferably conform to the width $W_T$ at the tips of the stent legs as seen in FIG. 5. The tabs extend both vertically down the stent leg for a distance $H_{t1}$, FIG. 6, and toward the center of the aperture defined by the stent ring for a distance $T_t$.

The exact dimensions of the tabs $W_t$, $H_{t1}$, $H_{t2}$ and $T_t$ in FIGS. 5 and 6, are, within the parameters of this invention, matters of design choice. The strength of material used in constructing the stent will affect the choice. Typical dimensions in the preferred embodiment are given in Table I below.

The tabs 120, 123 and 125 have apertures 121 formed therein through which the coaptation stitches pass. It is preferred that the coaptation stitches be passed through the holes 121 in the tabs since this registers the position of the coaptation stitch at a positive, repeatable location. The diameter of the holes 121 in the preferred embodiment is 0.813 mm, and the dimension $T_t$ in FIG. 6 is chosen to give sufficient strength. The use of holes 121 in the tabs located as described above insures good repeatability of manufacture because different assembly workers cannot change the orifice diameter or induce stresses in the tissue by inadvertent mislocation of the coapation stitch too far toward or away from the center of the aperture.

All the known stent material can be used in the stent 102 including but not limited to titanium, Delrin, polyacetal, polypropylene, and Elgiloy. The tabs 120, 123 and 125 are included in the preferred embodiment because they have been found to be highly desirable and necessary, in many instances, for sufficient strength; however, the tabs are not always necessary. With refined manufacturing techniques and adaptation of stronger materials, tabs are expected to be eliminated or reduced in size. The fundamental concept disclosed herein is extension of the service life of the valve by reducing stress levels in the tissue by, among other things, utilizing narrower, rounded stent leg tips 107, 109 and 111 shown in FIGS. 3 and 4. Ideally, a substantially zero tip width is desirable, but structurally this is impossible at present. The width of the stent leg at its tip is made more narrow than heretofore known; however, the stated width of the tips of the stent legs in the preferred embodiment should not be understood as limiting the invention in any way.

A general guideline for the narrowness of the stent leg tip is that the tip should be sufficiently narrow so that the quotient of the radius of curvature of tissue together inside the stent leg tip divided by the thickness of the tissue is greater than or equal to five. The radius of curvature $R_c$ of the tissue inside a typical stent leg tip is illustrated in FIG. 4. This curvature is caused by the coaptation of the leaflets under pressure and tends to concentrate shear stresses in the tissue at points 135 and 137 where curvature is greatest. In the preferred embodiment, this ratio should be a minimum of approximately five. That is, if the radius of curvature of the tissue around the tip of the stent leg is less than approximately five times the thickness T of the tissue, then the tips of the stent legs are too wide. This general guideline has been shown to increase the service life of the valve; but the foregoing statement should not be understood as limiting the invention to a ratio of five.

It is critical that the stent dimensions be selected such that touching between the tissue and the stent be substantially eliminated or minimized, and the radius of curvature of the tissue around the stent not be smaller than a predetermined value. That is, touching between the tissue and the stent is substantially eliminated or minimized, and the radius of curvature of the tissue around the stent measured at the point of greatest curvature divided by the thickness of the tissue should be greater than or equal to five. This curvature at two of the various places on the stent where it occurs is illustrated in FIGS. 4 and 10. FIG. 4 is a sectional view taken along section line 4—4 in FIG. 2 looking down on the top of the stent leg. The center of the stent is toward the top of FIG. 4. The radius lines $R_c$ illustrate the radius of curvature of the tissue 21 together inside the stent leg tip 107 and the fabric covering 113 surrounding the tip. The coaptation stitch 134 is seen to pass through the hole 121 in the stent leg tip and is approximately centered above the tip of the leg. The points of maximum curvature 135 and 137 are seen to be in the tissue at a point just inside of the centermost extremity of the cloth covering 113. The thickness of the tissue is designated T. The ratio of $R_c/T$ should be greater than or equal to five for extended durability.

FIG. 10 is another sectional view of a place of curvature of the tissue around the stent taken along section line 10—10 in FIG. 2. Again, $R_c$ indicates the radius of curvature of the tissue 21 over the top of the cloth covering 124 surrounding the base ring 104 of the stent. T indicates the thickness of the tissue and, for extended durability the ratio $R_c/T$ should be greater than or equal to five.

The reason for the above stated criteria of tip narrowness is that most curvature of the tissue around the stent leg occurs at the tips 109, 111 and 113 of the stent leg where the coaptation stitches 132, 130 and 134 in FIG. 1 pull the cusps together. Thus, stress in the tissue is concentrated where the radius of curvature is smallest as can be visualized in examining FIGS. 7 and 4. Because the tissue formed around the post and inside of the coaptation stitches is mobile, a large radius through which the tissue can flex helps to reduce the risk of fatigue failures.

Figure 11:
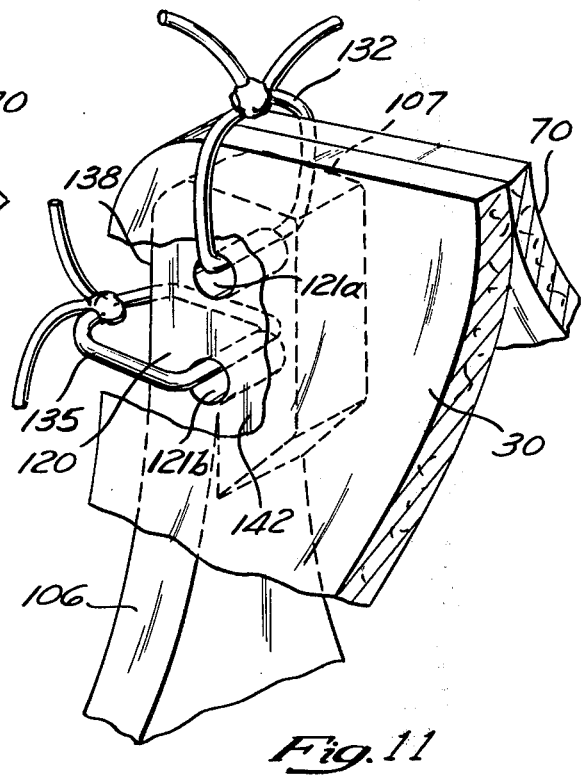
FIG. 11 is a detailed view of another embodiment of the coaptation stitching.

Referring to FIG. 11, there is shown another embodiment of a coaptation stitch arrangement typical for all three stent legs. This embodiment includes a separate coaptation stitch 132 passing through the tissue leaflets 30 and 70, through the top hole 121a in the tab 120, and up and over the tip 107 of the stent leg 106. Coaptation stitch 132 could be a group of stitches. Another coaptation stitch 135, or group of stitches, passes through the tissue leaflets 30 and 70, through the bottom hole 121b in the tab 120 and out and around the outside of the stent leg 138. Thus, the top coaptation stitch 132 lies in a plane parallel to the long axis of the stent leg 106. The top stitch 132 or group of stitches is tied off above the tip 107 of the stent leg. The bottom coaptation stitch 135 lies in a plane generally perpendicular to the plane of the top stitch or stitches 132 and is tied off at the outside edge 138 of the stent leg 106. These stitches are placed so that they do not interfere with normal operation in the open position.

Because the thread is smaller in diameter than the holes 121, the thread of coaptation stitches 132 and 135 will pull to the side of the holes 121 closest to the stitch knot when the thread is pulled tight. At times during manufacture, the thread may not be passed through the tissue leaflets along an axis parallel to the axis of the bottom hole 121b. Thus, when the thread is pulled tight the tissue leaflet on one side of the hole is moved farther toward the knot at the outside edge 138 of the stent leg than is the tissue leaflet on the other side. Thus uneven pulling can cause wrinkling of the tissue leaflets.

An improvement of the coaptation stitching of FIG. 11 is illustrated in FIG. 12 which shows the preferred embodiment of the coaptation stitching arrangement. FIG. 12 shows a coaptation stitch or stitches 140 residing generally in a plane parallel to the long axis of the stent leg and passing through both the top and bottom holes 121a and 121b and through the tissue leaflets 30 and 70. The stitch can be either a single figure eight stitch as shown in FIG. 12 or it can be two separate stitches, each passing through both tissue leaflets and through one of the holes 121a or 121b. Each stitch 140 is tied together above the tip 107 of the stent leg 106. The figure eight stitch shown in FIG. 12 is the preferred embodiment however because it is simpler and faster to implement than two separate stitches both in a vertical plane. The figure eight stitch is simpler because only one knot need be tied.

The coaptation stitch illustrated in FIG. 12 tends to eliminate the tendency for variations in stitch placement during manufacturing which can cause wrinkling of the tissue leaflets.

Referring again to FIG. 12, it has been found experimentally that the width, $W_T$, of the tab and the amount of inward projection or protruberance, P, of the tab from the inside edge of the hole toward the center of the aperture is important in preventing abrasion of the tissue leaflets on the inside edges of the tab. When the tissue leaflets coapt together during the closing action of the valve, if the tabs 120, 123 and 125 protrude too far in toward the center of the aperture, abrasion can occur in the area generally marked 142 in FIG. 8. To prevent this abrasion, the dimension P shown in FIGS. 5 and 12 is, in the preferred embodiment, restricted to a maximum of forty thousandths of an inch of (0.040 inches or 1.016 millimeters). However, any embodiment will be satisfactory wherein the distance which the tab extends toward the center of the aperture is restricted to a distance which substantially eliminates touching between the tissue leaflets and the bottom surfaces or lower 20% of the tab under maximum backpressure conditions. The bottom of the tab surfaces refers generally to those portions of the tab surface below the midway point in the height of the tab designated $H_{T2}$ in FIGS. 6, 13 and 14.

The area of coaptation of the tissue leaflets, designated generally as 144 in FIG. 8, tends to grow larger during higher backpressure conditions. This phenomenon can be visualized by placing the fingertips one each hand together fingerprint to fingerprint with the fingertips on the other hand to form a roof shaped arrangement. The fingerprint area of contact represents the area of coaptation 144 in FIG. 8. As the hands are pressed together keeping the fingers stiff, the fingers tend to flex toward each other such that the opposing first and second knuckle areas tend to come closer together. This represents the situation when higher backpressure exists on the tissue leaflets during closing.

As the tissue leaflets come closer together under increased backpressure, the area of contact between the leaflets tends to increase by expanding in the downward direction i.e. toward the stent ring 104 in FIG. 7. If the tabs 120, 123 and 125 extend too far in toward the center, abrasion between the mobile areas of the tissue leaflets just inside the tabs and the bottom portions of the tabs can occur. Restriction of the distance which the tabs protrude into the aperture tends to eliminate the aforestated abrasion.

Figure 13:
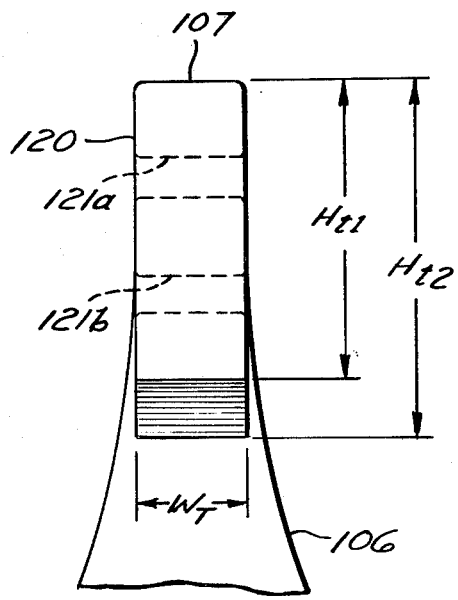
FIG. 13 is a detailed view of a typical tab and stent leg tip showing the relative widths of each.

The same reasoning applies to restriction of the relative widths, $W_T$, of the tabs 120, 123 and 125 throughout their height $H_{T2}$ as compared to the relative width of the stent legs 106, 108 and 110 as the stent legs descend from tips 107, 109 and 111. Referring to FIG. 13, there is shown a detail view of the preferred embodiment for the tabs and stent leg tips. As seen in FIG. 13, the width, $W_T$, of the tab 120 remains constant throughout its height $H_{T2}$, regardless of the width of the stent legs. It is seen in FIG. 13 that the width of the stent leg 106 is increasing at points farther away from the tip 107.

Figure 14:
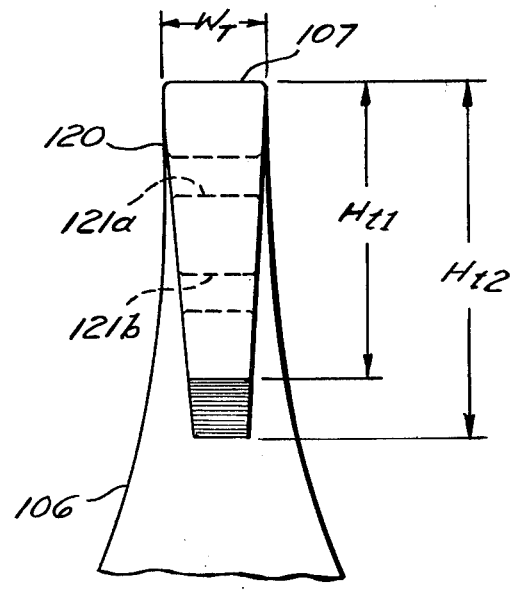
FIG. 14 is a detailed view of another embodiment of a typical tab and stent leg tip showing the relative widths of each.

FIG. 14 show another embodiment for the tabs wherein the width, $W_T$, of the tab decreases at points farther down from the tip 107 irrespective of the width of said stent legs.

The purpose of maintaining a constant or decreasing width for the tabs 120, 123 and 125 is to minimize the possibility of abrasion of the tissue leaflets on the tabs during closure of the valve and coaptation of the tissue leaflets just inside the tabs. The increasing width of the stent legs 106, 108 and 110 tend to give shape and support to the tissue leaflets to form the cusps of the valve. The increasing width of the stent legs versus the constant or decreasing width of the tabs tends to keep the tissue leaflets away from the lower surfaces of the tabs during coaptation thereby minimizing abrasion. Any shape or form for the tabs which accomplishes the purpose of minimizing or eliminating this abrasion will be satisfactory and is intended to be included within the scope of the claims appended thereto.

As exemplary only and not in any limiting sense, optimum stent dimensions for the stent depicted in FIGS. 5 and 6 are given in Table I. In FIGS. 5 and 6, $D_i$ refers to the inside diameter of the stent ring and $D_o$ refers to the outside diameter thereof. U refers to the depth of scallop 112 and W refers to the width of stent ring 104. $R_i$ refers to the inside radius of the scallop 112 and $R_o$ refers to the outside radius of the scallop forming the bottom of stent ring 104. Finally, $H_{T2}$ refers to the total height of the tabs.

It will be apparent that the foregoing description, given in detail as to the method of carrying out the best mode of invention as contemplated by the inventor, is given to exemplify the concepts and principles of the invention and not to limit it. Similarly, the structures and elements of the invention have been described, in their best mode embodiments, as integral, in the case of the stent, and separate, in the case of the leaflets. However, whether formed of one or many pieces, if the structure which results functions in the manner as described herein, it is the same invention. Thus, it is contemplated that the scope of the invention will be as defined in the following claims read in light of the principles of the invention as disclosed herein and not limited by the best mode.

INDUSTRIAL APPLICATION

The present invention will find the greatest application in the manufacture of heart valve prostheses in the medical and surgical profession.

TABLE I

| Nominal Valve Size | STENT DIMENSIONS (mm) | | | | |
|---|---|---|---|---|---|
| | Outside Diameter $D_o$ (FIG. 5) | Inside Diameter $D_i$ (FIG. 5) | Height H (FIG. 6) | Ring 104 Thickness T (FIG. 5) | Ring 104 Width W (FIG. 6) |
| 15 | 13.51 | 11.99 | 10.41 | 0.762 | 2.67 |
| 17 | 15.49 | 13.97 | 11.43 | 0.762 | 2.67 |
| 19 | 17.53 | 16.00 | 12.45 | 0.762 | 2.92 |
| 21 | 19.56 | 17.78 | 13.46 | 0.889 | 2.92 |
| 23 | 21.336 | 19.56 | 14.48 | 0.889 | 2.92 |
| 25 | 23.37 | 21.34 | 15.75 | 1.016 | 3.18 |
| 27 | 25.40 | 23.36 | 16.76 | 1.016 | 3.18 |
| 29 | 27.30 | 25.02 | 18.03 | 1.143 | 3.43 |
| 31 | 29.51 | 27.23 | 19.25 | 1.143 | 3.43 |
| 33 | 31.24 | 28.96 | 20.62 | 1.143 | 3.68 |

| Scallop Depth U (FIG. 6) | Inside Radius $R_i$ (FIG. 6) | Outside Radius $R_o$ (FIG. 6) | Post Top Width $W_T$ (FIG. 5) | "U"/"$D_i$" | Tab Thickness $T_T$ (FIG. 6) | Tab Height $H_{T1}$ | $H_{T2}$ (FIG. 6) |
|---|---|---|---|---|---|---|---|
| 7.74 | 5.13 | 7.42 | 0.761 | 0.646 | 1.65 | 2.79 | 3.56 |
| 8.76 | 6.07 | 8.36 | 0.761 | 0.627 | 1.65 | 2.79 | 3.56 |
| 9.53 | 6.93 | 9.47 | 0.761 | 0.596 | 1.65 | 2.79 | 3.56 |
| 10.54 | 7.72 | 10.26 | 0.889 | 0.593 | 1.78 | 3.20 | 4.06 |
| 11.56 | 8.28 | 10.82 | 0.889 | 0.591 | 1.78 | 3.63 | 4.57 |
| 12.57 | 9.53 | 12.32 | 1.016 | 0.589 | 1.78 | 4.04 | 5.08 |
| 13.59 | 10.29 | 13.08 | 1.016 | 0.582 | 1.78 | 4.44 | 5.59 |
| 14.61 | 11.20 | 14.25 | 1.016 | 0.584 | 1.90 | 4.85 | 6.10 |
| 15.82 | 12.19 | 15.24 | 1.14 | 0.581 | 1.90 | 5.28 | 6.60 |
| 16.94 | 13.21 | 16.51 | 1.14 | 0.585 | 2.03 | 5.69 | 7.11 |

What is claimed is:

1. A stent for a tissue heart valve having tissue cusps and coaptation stitches, said stent for reducing stress in the tissue of the cusps comprising:
   a ring with scallops formed therein defining an aperture with inflow and outflow ends; and
   a plurality of legs coupled to said ring and extending upwardly toward said outflow end each said leg dimensioned such that the radius of curvature of mobile tissue around and near the stent measured at the point of greatest curvature divided by the thickness of the tissue is greater than or equal to five at all points of contact between said tissue and said stent.

2. The stent of claim 1 further including inwardly projecting tab means at outflow end of each stent leg for adding structural strength to said legs.

3. The stent of claim 2 further including means on said tabs means coupled to said coaptation stitches for fixing the location of said stitches.

4. The stent of claim 3 wherein said means for coupling to said coaptation stitches is a plurality of holes through said tab means.

5. A tissue prosthetic heart valve comprising:
   (a) a stent comprising:
      (1) a ring with scallops formed therein defining an aperture with inflow and outflow ends; and
      (2) a plurality of legs coupled to said ring extending upwardly toward said outflow end, each said leg dimensioned such that the quotient of the radius of curvature of mobile tissue inside and around said stent measured at the point of greatest curvature divided by the thickness of said tissue is greater than or equal to five at all points of contact between said tissue and said stent;
   (b) a plurality of tissue leaflets attached to said stent and to each other to form a valving element; and
   (c) a plurality of coaptation means for causing joining of the edges of said tissue leaflets in the vicinity of the tips of said stent legs.

6. The prosthetic heart valve of claim 5 further including inwardly projecting tab means at the outflow end of each stent leg for adding structural strength to said legs.

7. The prosthetic heart valve of claim 5 further including means on said tab means coupled to said coaptation means for fixing the location of said stitches.

8. The valve of claim 7 wherein said means for fixing the position of said coaptation means comprises a plurality of holes through said tab means.

9. The valve of claim 8 wherein said coaptation means comprises a plurality of stitches a first group of which lies in a plane generally parallel to the long axis of said stent legs and which are tied off above the tips of said stent legs, and a second group of which lies in a plane generally perpendicular to the plane of said first group and which are tied off at the outside edge of said stent legs.

10. The valve of claim 8 wherein said coaptation means is a plurality of stitches lying generally in a plane parallel to the long axis of the stent leg and passing through said plurality of holes and said tissue leaflets and which are tied off above the tips of said stent legs.

11. The valve of claim 10 wherein each said tab has two holes therein and wherein said coaptation stitches define figure eight patterns through said holes.

12. The valve of claim 6 wherein the distance that said tab means projects inwardly toward the center of said aperture is restricted to a distance which substantially eliminates touching between the tissue leaflets and the bottom surfaces of said tab means.

13. The valve of claim 8 wherein the distance that said tab means project inwardly toward the center of said aperture from the edge of said holes closest to the center of said aperture is restricted to a distance which substantially eliminates touching between the tissue leaflets and the bottom of said tabs means.

14. The valve of claim 8 wherein the distance that said tab means projects inwardly toward the center of said aperture from the edge of said holes closest to the center of said aperture is a maximum of forty thousandths of an inch for the uncovered stent.

15. The valve of claim 6 wherein the widths of said tab means remains constant throughout its height irrespective of the width of said stent legs.

16. The valve of claim 6 wherein the width of said tab means remains constant throughout its length while the width of said stent legs increases at points farther from the tips of said stent legs.

17. The valve of claim 8 wherein the width of said tab means decreases at points farther from the tips of said stent legs irrespective of the width of said stent legs.

* * * * *